(12) United States Patent
Yodfat et al.

(10) Patent No.: US 9,028,409 B2
(45) Date of Patent: May 12, 2015

(54) FLUID DELIVERY WITH IN VIVO ELECTROCHEMICAL ANALYTE SENSING

(75) Inventors: Ofer Yodfat, Maccabim-Reut (IL); Gavriel J. Iddan, Haifa (IL); Ruthy Kaidar, Haifa (IL); Gali Shapira, Haifa (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 375 days.

(21) Appl. No.: 11/963,481

(22) Filed: Dec. 21, 2007

(65) Prior Publication Data

US 2008/0214916 A1 Sep. 4, 2008

Related U.S. Application Data

(60) Provisional application No. 60/876,945, filed on Dec. 22, 2006.

(51) Int. Cl.
| | |
|---|---|
| *A61B 5/05* | (2006.01) |
| *A61B 5/145* | (2006.01) |
| *A61B 5/1486* | (2006.01) |
| *A61M 5/172* | (2006.01) |
| *A61B 5/1495* | (2006.01) |
| *A61M 5/142* | (2006.01) |

(52) U.S. Cl.
CPC ......... *A61B 5/14532* (2013.01); *A61B 5/14865* (2013.01); *A61B 5/1495* (2013.01); *A61M 2005/14268* (2013.01); *A61M 5/1723* (2013.01); *A61M 2205/50* (2013.01); *A61M 2230/201* (2013.01); *A61M 5/14248* (2013.01)

(58) Field of Classification Search
USPC .......................................... 600/345, 347, 365
See application file for complete search history.

(56) References Cited

U.S. PATENT DOCUMENTS

| | | | |
|---|---|---|---|
| 2,631,847 A | 3/1953 | Hornberger et al. | |
| 3,771,694 A | 11/1973 | Kaminski | |
| 4,403,984 A * | 9/1983 | Ash et al. ...................... | 604/503 |
| 4,449,843 A | 5/1984 | Wendel | |
| 4,544,369 A | 10/1985 | Skakoon et al. | |
| 4,657,486 A | 4/1987 | Stempfle et al. | |
| 4,671,288 A * | 6/1987 | Gough ........................... | 600/347 |
| 4,685,463 A * | 8/1987 | Williams ...................... | 600/365 |
| 5,097,834 A | 3/1992 | Skrabal | |
| 5,390,671 A | 2/1995 | Lord et al. | |
| 5,957,895 A | 9/1999 | Sage et al. | |

(Continued)

FOREIGN PATENT DOCUMENTS

| | | |
|---|---|---|
| EP | 1 153 571 A | 11/2001 |
| JP | 03-505821 | 12/1991 |

(Continued)

OTHER PUBLICATIONS

International Search Report for related patent PCT/IL07/001579 performed by International Searching Authority/EP on Apr. 8, 2008.

*Primary Examiner* — Michael D'Angelo
(74) *Attorney, Agent, or Firm* — Dinsmore & Shohl LLP

(57) ABSTRACT

One or more therapeutic fluids, such as for example insulin can be delivered to a body. In addition or alternatively, the concentrations of one or more analytes can be measured in vivo. A feedback process can be used to regulate levels of the one or more analytes based on the measurements via delivery of the one or more therapeutic fluids. Related systems, apparatus, methods, and/or articles are also described.

25 Claims, 18 Drawing Sheets

(56) References Cited

U.S. PATENT DOCUMENTS

| | | | |
|---|---|---|---|
| 5,993,411 A * | 11/1999 | Choi | 604/67 |
| 6,275,717 B1 * | 8/2001 | Gross et al. | 600/345 |
| 6,485,461 B1 | 11/2002 | Mason et al. | |
| 6,589,229 B1 * | 7/2003 | Connelly et al. | 604/890.1 |
| 6,612,111 B1 | 9/2003 | Hodges et al. | |
| 6,723,072 B2 | 4/2004 | Flaherty et al. | |
| 6,740,059 B2 | 5/2004 | Flaherty | |
| 2003/0130616 A1 * | 7/2003 | Steil et al. | 604/66 |
| 2006/0001550 A1 | 1/2006 | Mann et al. | |
| 2006/0020191 A1 * | 1/2006 | Brister et al. | 600/345 |
| 2006/0224141 A1 * | 10/2006 | Rush et al. | 604/503 |
| 2006/0263839 A1 | 11/2006 | Ward et al. | |
| 2008/0004515 A1 * | 1/2008 | Jennewine | 600/345 |

FOREIGN PATENT DOCUMENTS

| | | |
|---|---|---|
| WO | WO-9614026 A1 | 5/1996 |
| WO | WO 01/58348 A | 8/2001 |
| WO | WO-2006102412 | 9/2006 |
| WO | IL2006/001276 | 11/2006 |
| WO | WO 2006/124759 A2 | 11/2006 |
| WO | WO 2006/124759 A3 | 11/2006 |

* cited by examiner

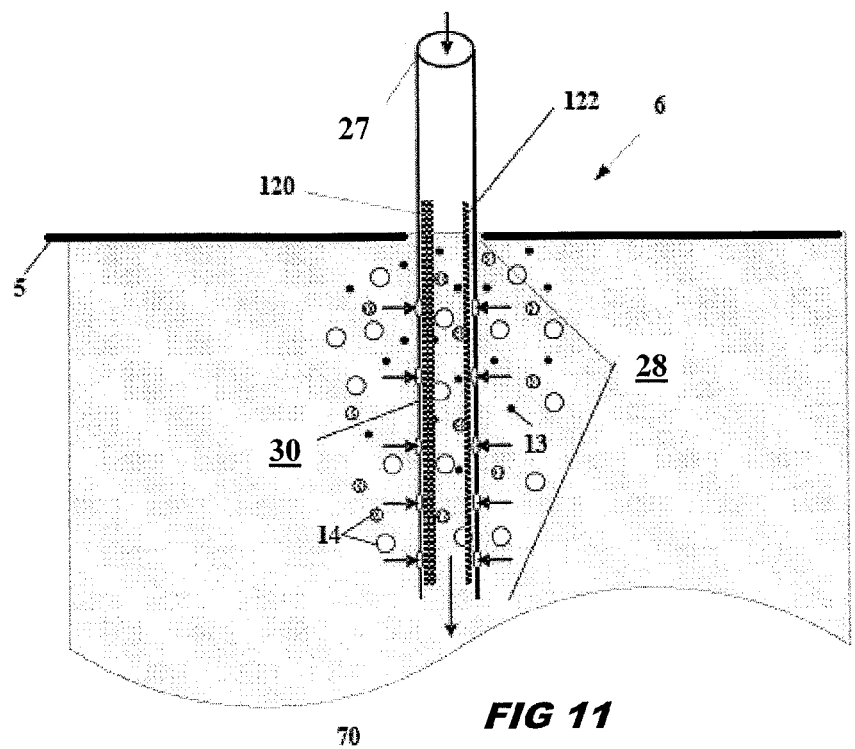
FIG 11
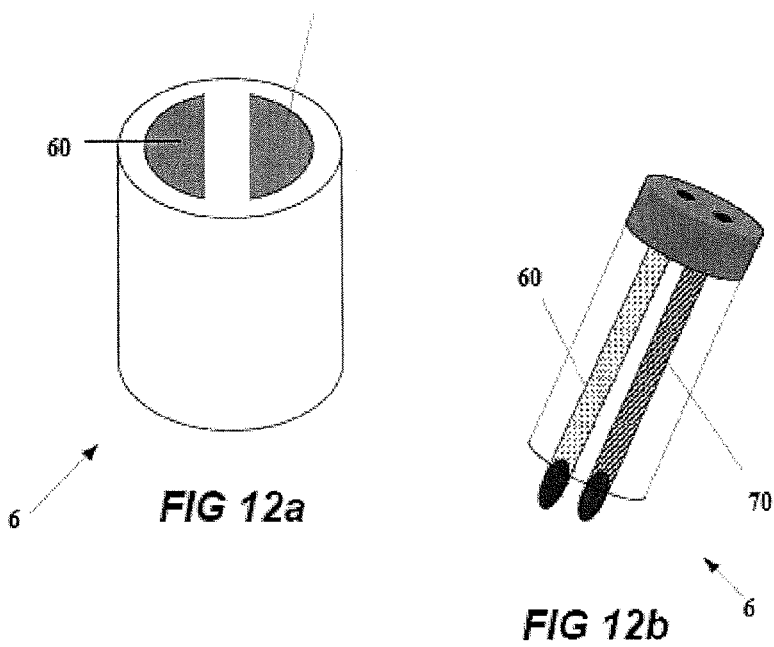
FIG 12a
FIG 12b

FLUID DELIVERY WITH IN VIVO ELECTROCHEMICAL ANALYTE SENSING

CROSS-REFERENCE TO RELATED APPLICATIONS

This application claims the benefit of U.S. Provisional Patent Application Ser. No. 60/876,945, filed on Dec. 22, 2006 and entitled "Fluid Delivery Device Capable of in Vivo Electrochemical Sensing of Analyte" which is incorporated by reference herein in its entirety.

FIELD

The subject matter described herein relates to delivery of a fluid via a device or other mechanisms that is also capable of in vivo sensing of one or more analytes.

BACKGROUND

Diabetes mellitus is a disease of major global importance, and its frequency of incidence has been increasing at almost epidemic rates. The worldwide prevalence in 2006 was 170 million people, and this number is predicted to at least double over the next 10-15 years. Diabetes is generally characterized by a chronically raised blood glucose concentration (hyperglycemia), due to a relative or absolute lack of the pancreatic hormone, insulin. In a normal (non-diabetic) subject, pancreatic islet cells (beta cells) continuously sense the blood glucose levels and consequently regulate insulin secretion to maintain near constant levels. However, diabetic patients lack this capability.

Much of the burden of the disease to the patient and to health care resources is due to long-term tissue complications, which can affect both the small blood vessels (microangiopathy, causing eye, kidney and nerve damage) and the large blood vessels (causing accelerated atherosclerosis, with increased rates of coronary heart disease, peripheral vascular disease and stroke). There is now evidence that morbidity and mortality of diabetic patients is related to the duration and severity of hyperglycemia. In theory, maintaining normal blood glucose levels by hormone replacement therapy using insulin injections and/or other treatments in diabetes might be able to prevent complications. However, near-normal blood glucose levels can be quite difficult to achieve and maintain in many patients, particularly in those having Type 1 diabetes. In these patients, blood glucose concentrations can vary fairly quickly between very high (hyperglycemia) and very low (hypoglycemia) levels in an unpredictable manner.

Many diabetic patients currently measure their own blood glucose several times during the day by using finger-prick capillary samples and applying the blood to a reagent strip for analysis in a portable glucose meter. The discomfort involved with these tests can often lead to poor patient compliance. Testing cannot be performed while sleeping and while the subject is occupied. In addition, the readings do not give information regarding the trends in glucose levels, but rather provide only discrete readings, taken at large time intervals between the measurements. Therefore continuous glucose monitoring would be advantageous, providing essentially continuous glucose readings by performing discrete measurements, at a very high frequency.

An electrochemical glucose sensor is described in U.S. Pat. No. 6,612,111 assigned to Lifescan Inc., which is hereby incorporated by reference herein. Today, the majority of available electrochemical glucose sensors are enzyme-based. The detection principle of these sensors is based on the monitoring of the enzyme-catalysed oxidation of glucose. These include glucose sensors use amperometric or potentiometric operating principles.

The enzymatic reaction that occurs in the majority of these sensors is catalyzed by glucose oxidase (GOX). During this reaction, oxygen and glucose yield gluconic acid and hydrogen peroxide. Glucose oxidase acts temporarily as an electron acceptor, where it is first reduced to an inactive state and subsequently is reactivated by the reduction of oxygen to hydrogen peroxide. The glucose concentration is transformed into a detectable signal, which is proportional to the glucose level and which is generally measured by amperometric methods.

An enzyme-coated working electrode can serve as the sensor transducer, which is where electrochemical oxidation or reduction takes place. A counter electrode can be paired with the working electrode. A current of opposite sign passes through the two electrodes. The intensity of the current is a function of the concentration of electro-active glucose. An increased surface area between the analyte sensing layer (containing the enzyme) and the working electrode can enable enzyme loading, which is necessary for overcoming degradation of the enzyme as the reaction proceeds. The increased surface area can also enable enhanced electron transfer between the enzyme active site and the sensor transducer, thus improving the sensor performance.

Several ambulatory insulin infusion devices are currently available on the market. The first generation disposable devices configured as syringe-type reservoir are described in 1972, by Hobbs, in U.S. Pat. No. 2,631,847, and in 1973, by Kaminski, in U.S. Pat. No. 3,771,694, and later by Julius, in U.S. Pat. No. 4,657,486, and by Skakoon, U.S. Pat. No. 4,544,369, each of which is hereby incorporated by reference herein. These devices are generally quite large and heavy due to their spatial design and the relatively large driving mechanism of the syringe and the piston. This relatively bulky device has to be carried in a patient's pocket or attached to the belt. Consequently, the fluid delivery tube can be quite long, in some cases grater than 40 cm, to permit needle insertion in remote sites of the body. Such uncomfortable, bulky fluid delivery devices can be rejected by many diabetic insulin users, because of their negative impact on the performance of regular activities, such as for example sleeping and swimming. Furthermore, some more self-conscious users, such as for example teenagers, are likely to reject the use of such a device because of the potential negative body image that might result from using it. In addition, the long delivery tube can exclude some potential remote insertion sites, such as for example the buttocks and the extremities.

To avoid potential disadvantages associated with tubing, a second generation of pumps based on a new concept has been devised. These pumps can include a housing having a bottom surface adapted for attaching to the user's skin, a reservoir disposed within the housing, and an injection needle in fluid communication with the reservoir. These skin adherable devices are generally disposed of every 2-3 days similarly to the infusion sets employed in the pumps of the first generation. Devices of this type have been described by Schneider, in U.S. Pat. No. 4,498,843, Burton in U.S. Pat. No. 5,957,895, Connelly, in U.S. Pat. No. 6,589,229, and by Flaherty in U.S. Pat. No. 6,740,059, each of which is incorporated by reference herein. Other configurations of skin adherable pumps are disclosed in U.S. Pat. Nos. 6,723,072 and 6,485,461, which are also incorporated by reference herein. The pumps described in these references are generally designed as a single piece and remain adhered to the user's skin for the entire usage duration. The needle emerges from the bottom surface of the device and is fixed to the device housing.

Another fluid delivery device is described in international patent application no. PCT/IL06/001276, which is currently and was at the time of the development of the current subject matter commonly owned with the present application and is incorporated by reference herein. This device is configured as a miniature portable, programmable, skin-adherable fluid dispenser, which does not employ long tubing. The device includes two parts: a disposable part and a reusable part. The reusable part includes the necessary electronic components along with driving and pumping mechanisms. The disposable part includes reservoir for therapeutic fluid, short delivery tube and exit port. This fluid delivery device can also include a remote control unit that allows data acquisition, programming, and user inputs. Even after connection of the reusable and disposable parts, the assembled device has a very thin dimension, rendering the whole device inexpensive, light, and discrete.

SUMMARY

In one aspect of the current subject matter, an apparatus includes a subcutaneously insertable element that includes a proximal portion and a distal portion. The distal portion is configured for subcutaneous placement within a human body. The apparatus also includes a sensor that electrochemically interacts with one or more analytes and generates a signal that is representative of a concentration of the one or more analytes. The sensor is disposed on or within the distal portion of the subcutaneously insertable element. A processor receives and processes the signal from the sensor to determine the concentration of the one or more analytes within the human body. An external device includes the processor and is in mechanical contact with the proximal portion of the subcutaneously insertable element.

Optional variations of the current subject matter can include one or more of the following features. The subcutaneously insertable element can optionally include a cannula having an internal volume and a wall surface. The cannula can optionally include a first electrode and a second electrode that is electrically isolated from the first electrode. The first electrode and the second electrode can optionally be secured to the cannula. The first electrode and the second electrode can optionally be disposed on an outer surface of the cannula. The wall surface of the cannula can optionally include a permeable or semi-permeable material that permits at least the one or more analytes to diffuse into the internal volume. The first electrode and the second electrode can optionally be disposed on an inner surface of the cannula. One or more of the first and second electrodes can optionally be disposed along at least part of a circumferential axis of the cannula or alternatively, along at least part of a longitudinal axis of the cannula. When the subcutaneously insertable element is placed subcutaneously, the sensor can optionally contact interstitial fluid. The sensor can optionally include a first electrode that has a first exposed surface that is at least partially coated with an electrochemical reagent and a second electrode that has a second exposed surface that is substantially free of the electrochemical reagent. The electrochemical reagent can optionally include an enzymatic assay that undergoes a chemical reaction with the one or more analytes, the chemical reaction producing a measurable voltage or current differential between the first electrode and the second electrode. The first and/or the second exposed surface can optionally include one or more surface area enlarging features.

The apparatus can optionally further include a reservoir that contains a fluid and a pump that flushes the subcutaneously insertable element with the fluid from the reservoir. The pump can optionally include a peristaltic pump or alternatively a syringe pump. The external device can optionally include a disposable part and a reusable part. The disposable part can optionally include the subcutaneously insertable element and the reusable part can optionally include the processor. The external device can optionally further include a delivery subsystem for a therapeutic fluid. The dispensing apparatus can optionally be controlled by the processor to deliver the therapeutic fluid in response to the concentration of the one or more analytes determined by the processor. The therapeutic fluid can optionally include insulin. The therapeutic fluid can optionally be delivered via the subcutaneously insertable element. The subcutaneously insertable element can optionally include a first lumen that comprises the sensor at the distal end of the subcutaneously insertable element and a second lumen through which the therapeutic fluid is delivered. Alternatively, the therapeutic fluid can optionally be delivered via a second subcutaneously insertable element. The processor can optionally automatically control the dispensing apparatus based on the determined concentration or, alternatively, the external device can provide an alert to a user to request that the user activate the dispensing apparatus based on the determined concentration. The sensor can optionally measure the concentration of the one or more analytes with a frequency that is either continuous, semi-continuous, periodic, or discrete.

The external device can also optionally further include a blood analysis device connected to the processor and a port via which a blood sample from the body is delivered to the blood analysis device. The blood analysis device can analyze the blood sample to independently determine the concentration of the one or more analytes and provide a calibration data point for the sensor. The blood analysis device can optionally include a glucometer. The one or more analytes can optionally include glucose. The external device can optionally include an adherable or securable surface that adheres or secures the device to the human body. The processor can optionally receive one or more commands from a remote control unit.

In an interrelated aspect, a method for fabrication of electrodes of a sensor on a surface of subcutaneously insertable element includes forming grooves on the surface of the subcutaneously insertable element, depositing conductive material within the grooves, temporarily covering at least one of the grooves to prevent contamination of the conductive material, depositing an electrochemical reagent on the uncovered position of the grooves, and removing the covering from the at least one of the grooves.

In another interrelated aspect, a method includes electrochemically detecting, with a sensor secured to a distal end of a subcutaneously insertable element, a concentration of an analyte within a human body, and based on the detecting, dispensing a therapeutic fluid to the human body.

In optional variations, one or more of the following features can be included. A device that comprises a processor and the subcutaneously insertable element can optionally be adhered or secured to a skin area of the human body such that the distal end of the subcutaneously insertable element is positioned beneath the skin surface and in contact with interstitial fluid of the human body. The electrochemical detection can optionally include generating a signal at the sensor that is representative of the concentration, and receiving and processing the signal at a processor in an external device that is mechanically connected to a proximal end of the subcutaneously insertable element. The dispensing of the therapeutic fluid can optionally include delivering a command from the processor to a dispensing apparatus in the external device. The command can optionally cause the dispensing apparatus to dispense an amount of the therapeutic fluid based on the determined concentration of the analyte in the human body. The dispensing of the therapeutic fluid optionally occurs via the subcutaneously insertable element. Alternatively, the dispensing of the therapeutic fluid optionally occurs via a second subcutaneously insertable element. Such devices can be closed loop, meaning that dispensing and sensing occur automatically or open loop or semi-open loop in which some user interaction is required before dispensing occurs.

The subject matter described herein can, in some implementations, provide one or more of the following advantages. For example, glycemic control can be achieved using a device or method that performs two important functions of a normal pancreas, namely glucose monitoring and insulin delivery. A closed loop system having a feedback mechanism combining both functions (often referred to as an "artificial pancreas") can be used to maintain near normal blood glucose levels in patients suffering from diabetes.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed embodiments. In the drawings.

FIG. 11 is a schematic diagram showing an example of a permeable cannula and the diffusion process;

FIG. 12a and FIG. 12b are schematic diagrams showing double lumen cannulae;

DETAILED DESCRIPTION

The current subject matter includes methods, systems, devices, apparatuses, techniques, and article of manufacture that can be used to provide improved fluid delivery and/or sensing and monitoring of analyte level(s) within a patient's body. A closed loop system configured for continuous, real-time monitoring of the analyte concentration levels in the body of a user can be provided. The monitoring can optionally be performed semi-continuously or with any other suitable frequency. In a closed loop system, near normal blood glucose levels can maintained due to delivery of insulin by a pump, such as for example a peristaltic pump, that is controlled in response to continuously, semi-continuously, or periodically monitored glucose levels. In this manner, an "artificial pancreas" can be provided to assist diabetic patients in living more normal lives.

Currently available closed loop systems are generally composed of two separate devices—a sensor and a pump—which can be expensive, bulky and heavy and are typically separately attached to the user's belt or skin. In addition, each of the two devices can require its own infusion set with long tubing and accordingly two insertion sites on the patient's body. It can be appreciated that the use of such a device could increase insertion and disconnection times and could produce undesirable effects like infections, irritations, bleeding, etc. As such, a need exists for an improved fluid delivery and/or sensing devices for delivering fluid to and/or monitoring analyte level(s) within a patient's body which is free of the above-mentioned drawbacks.

Figure 1A:
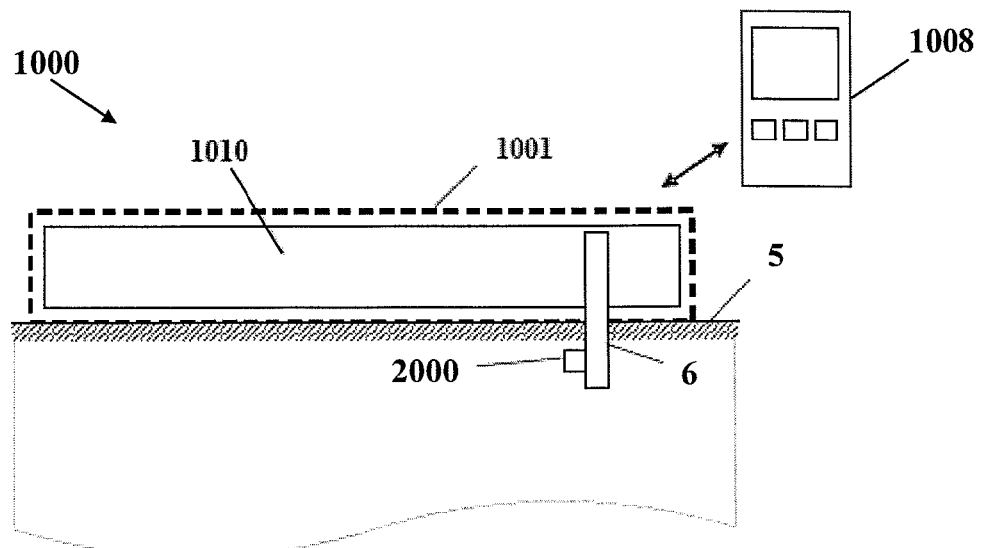
FIG. 1a and FIG. 1b are schematic diagrams showing examples of a fluid delivery device configured as a patch unit and a remote control unit.
Figure 1B:
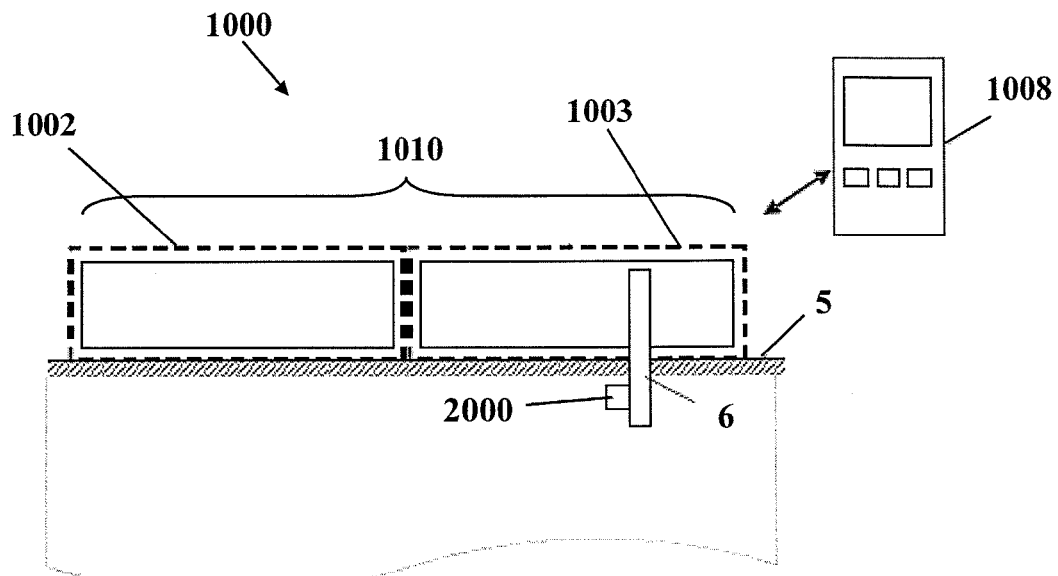

FIG. 1a and FIG. 1b show two possible implementations of devices 1000 according to the current subject matter. The device 1000 can include a patch unit 1010 that can be adhered to a user's skin 5, and a remote control unit 1008. The remote control unit 1008 can optionally be a single use device or alternatively be other command means like a multiple purpose computer or communication device such as for example a personal or laptop computer, or a handheld communication device (cell phone, personal data assistant, handheld wireless device, or the like).

Devices described herein and in accordance with the current subject matter can be capable of operating in one or more of a closed loop, and open loop, or a semi-open loop mode. In a closed loop mode, an analyte concentration is sensed by a sensor and determined by a processor and the processor commands a dispensing apparatus to dispense one or more therapeutic fluids to the human body based on the determined concentration. In an open loop mode, the sensing and dispensing functions are not linked. A device in this mode could indicate a value for the determined analyte concentration, but no feedback control is exercised over the rate of dispensing. A user interface or other means by which a user can communicate commands to the device can allow the user to dispense the therapeutic fluid. In the semi-closed mode, the sensing occurs as noted above for the closed loop mode. However, the device can wait for confirmation or alternatively it can request such confirmation, possibly via some user interface, from a user before dispensing the therapeutic fluid in the amounts that might be needed based on the determined analyte concentration.

A sensing element 2000 can be located subcutaneously, for example mounted on a subcutaneously insertable element, such as for example a cannula 6 that is inserted beneath the surface of the user's skin 5. For purposes of this disclosure, the terms "subcutaneously insertable element" and "cannula" will be used interchangeably. However, it will be understood that the term "cannula" does not limit the disclosed subject matter only to those subcutaneously insertable elements that fall within the dictionary definition of the word cannula. For example, in this disclosure, cannula includes both flexible and inflexible tubes that can be inserted into the body to either withdraw one or more body fluids or insert or inject therapeutic fluids including but not limited to medications, hormones, and the like. For example, the cannula can be made of a polymer material like Teflon™. Subcutaneously insertable elements or cannulae for the purposes of this disclosure can be of any shape, including but not limited to hollow cylinders of circular or non-circular cross-section. A cannula can have one or more distinct passages through which fluid can pass, and these passages can be arranged in any geometric orientation, including but not limited to one or more annular passages, one or more passages or lumens formed by dividing the cross section of the cannula into one or more similar or dissimilar volumes, two or more tubes running parallel through an otherwise non-porous element, or the like.

Various aspects of such subcutaneously insertable elements according to various implementations of the current subject matter are discussed in greater detail below. The patch unit can include a single part having one housing 1001 as shown in FIG. 1a or may include two parts having two separate housings 1002, 1003 as shown in FIG. 1b.

Figure 2:
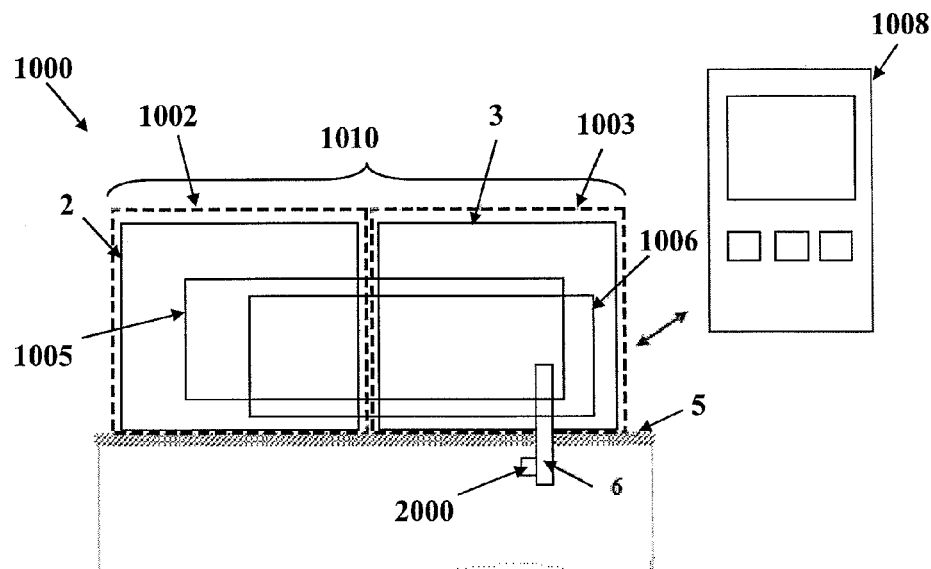
FIG. 2 is a schematic diagram showing an example of a fluid delivery device configured as a patch unit fitted with reusable and disposable parts residing in separate housings.

FIG. 2 shows additional detail of an implementation of a fluid delivery device 1000. The patch unit 1010 in this example includes two parts—a reusable part 2 and a disposable part 3. Each part has its own housing 1002, 1003. The device 1000 includes a sensing apparatus 1006 and a dispensing apparatus 1005. The relatively inexpensive components, such as for example the cannula 6 and the sensing element 2000 can advantageously be provided in the disposable part 3. The relatively more expensive components of both apparatuses, such as for example the electronics, etc., can be provided in the reusable part 2.

Figure 3:
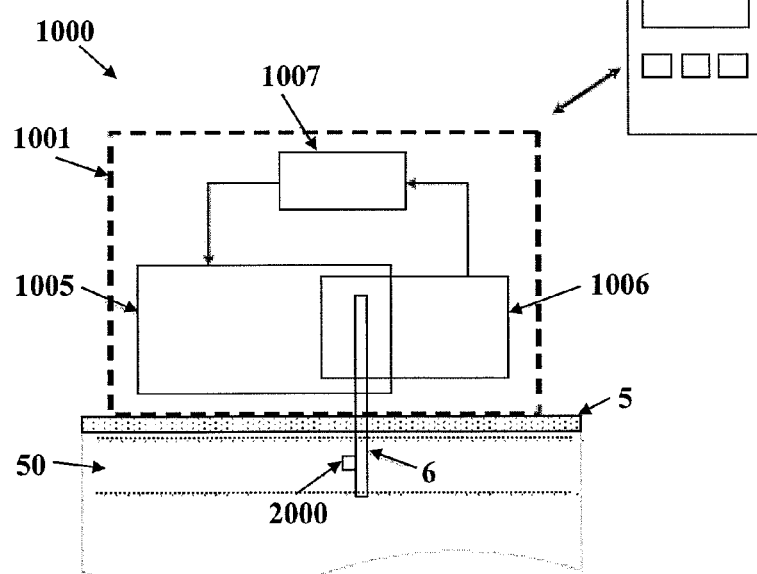
FIG. 3 is a schematic diagram showing an example of a closed loop system fitted with a single cannula and including a dispensing apparatus, and a sensing apparatus.

FIG. 3 shows another possible implementation of a device 1000, in which the dispensing apparatus 1005 and sensing apparatus 1006 are enclosed in a common housing 1001, and share a common single cannula 6 which can be inserted under the skin 5, to within the subcutaneous tissue 50. A cannula 6 that is shared between the sensing and dispensing function is referred to herein as dual function cannula. A processor-controller apparatus 1007 can also be provided within the housing 1001. The processor-controller apparatus 1007 can control dispensing of a fluid, such as for example insulin in accordance with the sensed concentration of an analyte, such as for example glucose. The analyte concentration can be obtained via the subcutaneously located sensing element 2000 provided at cannula 6. The device 1000 is capable of working as a closed-loop system. In another implementation, bidirectional communication between the processor-controller apparatus 1007 and a remote control unit 1008 can allow data acquisition, programming, and user inputs (such as for example meal carbohydrates). In this implementation, the device 1000 can also operate as a semi-closed loop system. The device 1000 can be attached to the user's skin 5 by adhesives (not shown). The dispensing apparatus can alternatively deliver insulin or some other fluid to the body by a separate trans-cutaneous means (not shown) in addition to or instead of a subcutaneous cannula 6. An example of such an alternative delivery system includes, but is not limited to, an array of miniature needles, which also can provide electrical and ultrasound skin stimulation.

Figure 4:
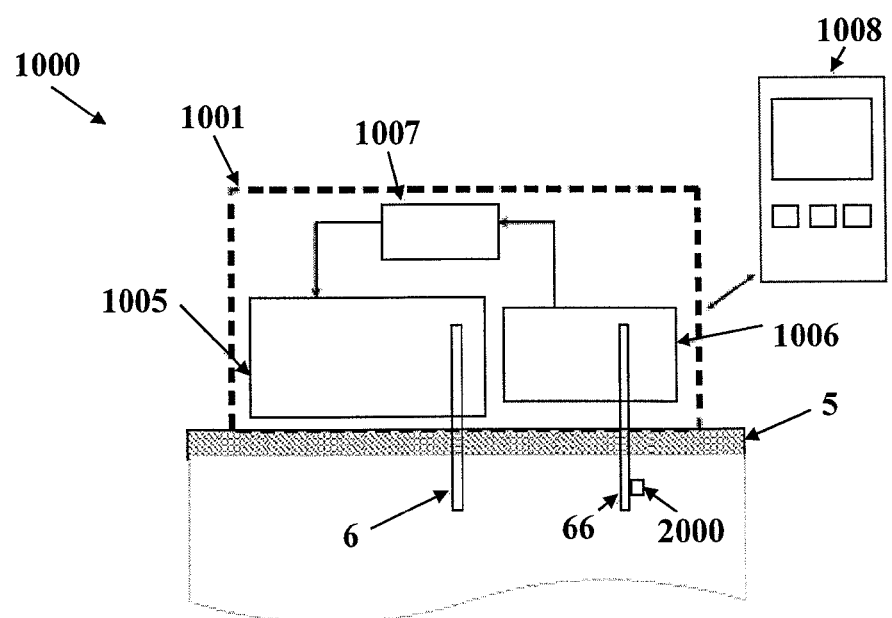
FIG. 4 is a schematic diagram showing an example of a closed loop system that includes a dispensing apparatus, a sensing apparatus, the processor-controller apparatus, and the remote control unit, in which the dispensing and sensing apparatuses have separate cannulae.

FIG. 4 shows another implementation of a device 1000 in which a dispensing apparatus 1005 delivers insulin by one cannula 6 and a sensing apparatus 1006 senses glucose by a subcutaneously located sensing element 2000 provided at another cannula 66. A processor-controller apparatus 1007 controls insulin delivery by the dispensing apparatus 1005 according to glucose levels sensed by the sensing apparatus 1006 and/or user inputs entered via the remote control unit 1008. In one variation, the two cannulae 6, 66 can be positioned apart from each other a some non-negligible distance.

Figure 5A:
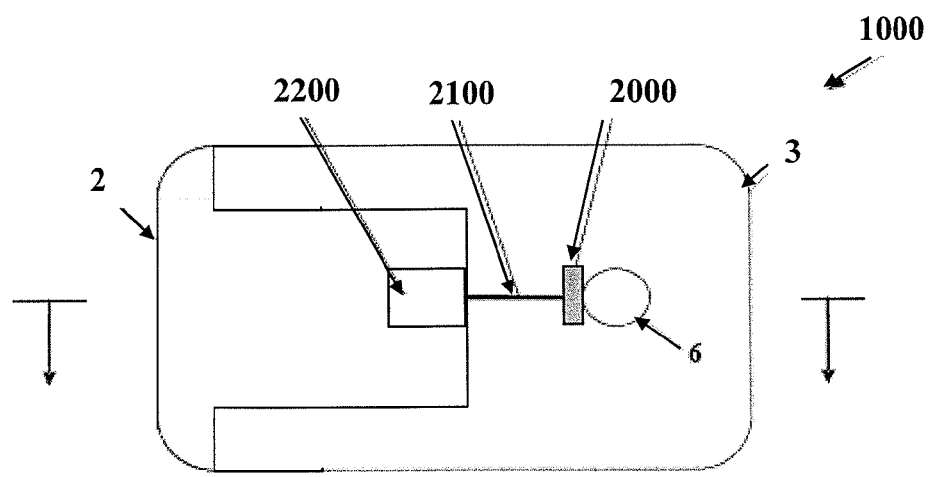
FIG. 5a and FIG. 5b are schematic diagrams showing a bottom view and a side cross-sectional view, respectively, of a fluid delivery device that includes a reusable part and a disposable part, with electrochemical sensing components deployed in these parts.
Figure 5B:
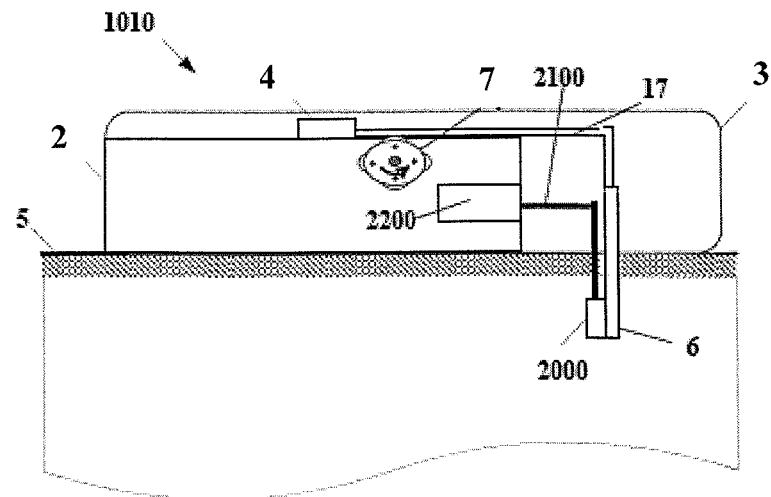

FIG. 5a and FIG. 5b show an implementation of the current subject matter in which a device 1000 is configured as a patch unit 1010 that includes two parts—a reusable part 2 and a disposable part 3. FIG. 5a shows a top view of the device 1000 and FIG. 5b shows a side view. The device 1000 can include delivery components such as a reservoir 4, a delivery tube 17 and a cannula 6, that are located within the disposable part 3, and a pumping mechanism 7 that is located within the reusable part 2. Sensing components can also be provided, for example a subcutaneously locatable sensing element 2000 that is located in the disposable part 3 and electrically connected by electrical wiring 2100 to a sensor processing element 2200 that is located within the reusable part 2.

Figure 6A:
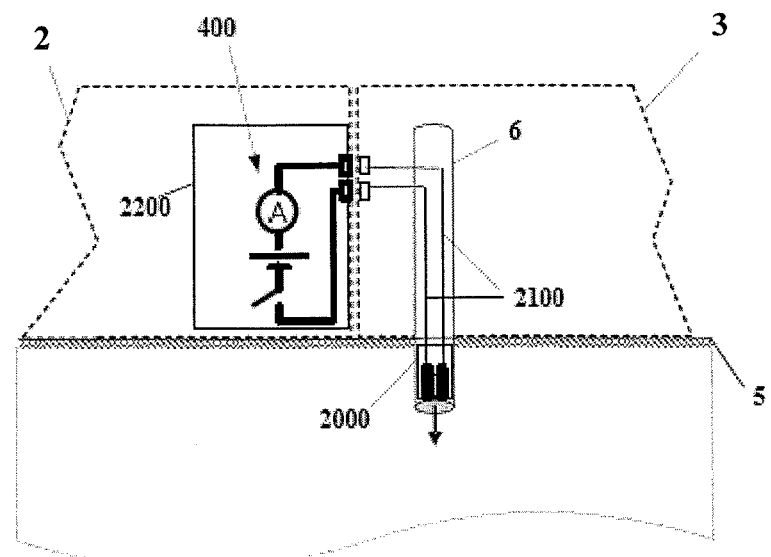
FIG. 6a and FIG. 6b are schematic diagrams showing a possible distribution of sensing apparatus components within the disposable and reusable parts of a device.
Figure 6B:
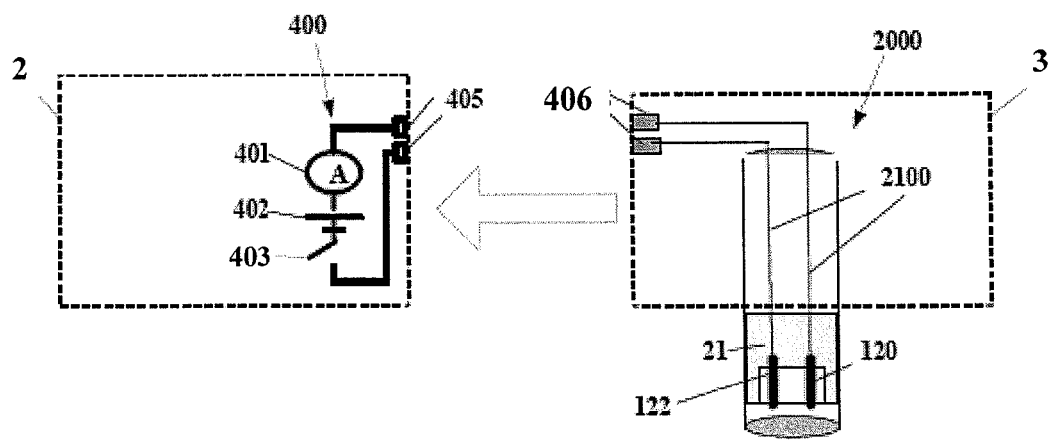

FIG. 6a and FIG. 6b show additional details regarding sensing components that can be employed in the fluid delivery device shown in FIG. 5a and FIG. 5b. The sensing components can be divided between the two parts of the patch unit 1010. FIG. 6a depicts the reusable part 2 and the disposable part 3 of the device 1000 connected to one another in an assembled configuration. FIG. 6b shows the reusable part 2 and the disposable part 3 of the device 1000 disconnected from one another. The sensing element 2000 can be located at the cannula 6 situated in the disposable part 3 and the sensor processing element 2200 is located in the reusable part 2. The sensor processing element 2200 can also include an amperometric circuit 400. Once the reusable part 2 and the disposable part 3 are connected, the amperometric circuit 400 is electrically closed, as shown in FIG. 6a.

As shown in FIG. 6b, an amperometer 401, a battery 402, a switch 403, and reusable part contacts 405 can be included in the reusable part 2. The disposable part 3 can include the sensing element 2000 which can include two or more electrodes 120, 122 that are optionally at least partially covered by or disposed within an insulating layer 21. The two or more electrodes 120, 122 can be connected to two disposable part contacts 406 with wiring 2100. The electrodes can be located at the cannula 6 of a device 1000 as discussed above and can in some variation reside within a portion of the cannula 6 that protrudes beneath the skin 5 when the device is affixed to the skin or otherwise worn by a user. The two or more electrodes can in some variations include a working electrode upon which an electrochemical, optionally enzymatic, reaction occurs, a counter electrode, that can be used to complete a circuit with the fluid with which the sensor is in contact, and optionally a reference electrode, that can be used to determine, by difference or otherwise, a voltage associated with the electrochemical reaction occurring at the working electrode.

When the amperometric circuit 400 is electrically closed by connecting the reusable part 2 and the disposable part 3, electrons flow from the working electrode 122 towards the positive pole of the battery 402. The amperometer 401 measures the flowing current. The switch 403 can control circuit operation.

Figure 7:
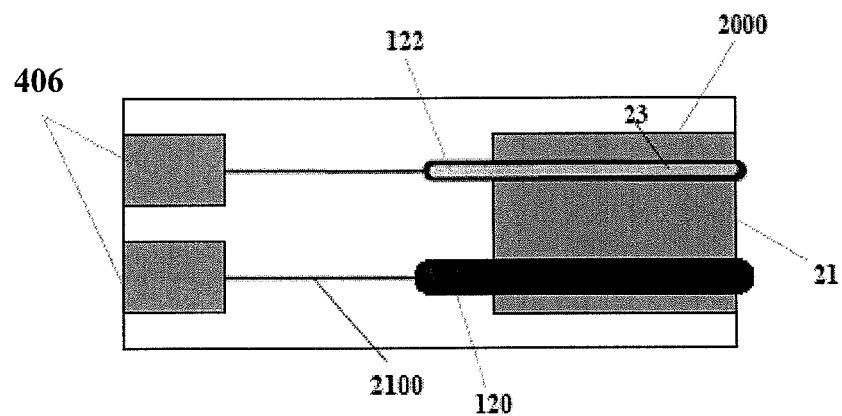
FIG. 7 is a schematic diagram showing additional detail of an example of a sensing element.

FIG. 7 shows additional detail regarding the sensing element 2000 and disposable part contacts 406. The sensing element 2000 can include at least 2 electrodes: one or more working electrodes 122, one or more counter electrodes 120 and optionally a reference electrode. The electrodes 120, 122 can be embedded within or otherwise covered by an insulating layer 21 deployed within or near the end of the cannula 6. The electrochemical reaction takes place on the working electrode 122 which can be at least partially covered by an analyte sensing layer 23. The analyte sensing layer can include the catalytic enzyme, and optionally a mediator and/or any other promoting components that might be desirable to enhance the enzymatic reaction. The promoting components can include those currently known in the art for promoting such reactions or other, new compounds or components. The analyte sensing layer 23 can in some variations be secured on the working electrode 122 by one or more suitable methods, such as for example cross-linking, entrapment, or the like. As noted above, the counter electrode 120 can be paired with the working electrode 122. A reference electrode can in some variations be used for measuring the working electrode potential. The generated signal associated with the sensed analyte concentration passes via wiring 2100 between the electrodes 120, 122 of the sensing element 2000 and the disposable part contacts 406.

Figure 8A:
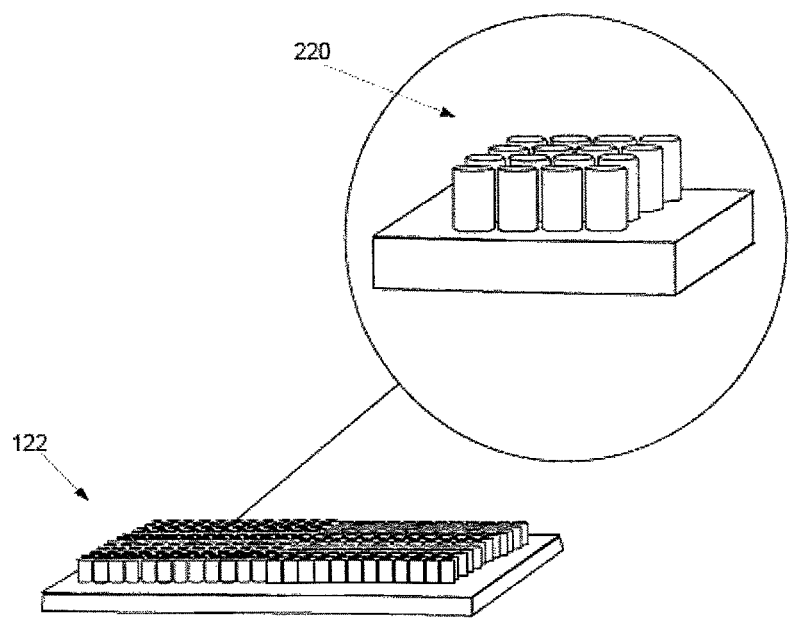
FIG. 8a and FIG. 8b are isometric diagrams showing examples of how the surface area of a working electrode can be increased.
Figure 8B:
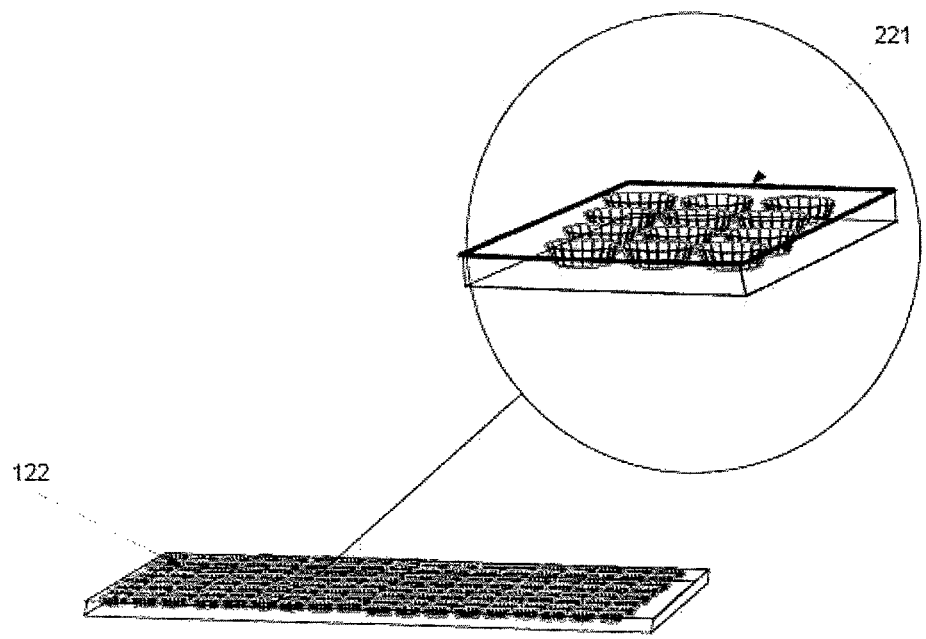

FIG. 8a and FIG. 8b show possible implementations of the working electrode 122, with surface area enlarging features to enhance the enzyme-analyte interactions. The surface area can be enlarged by inclusion of one or more artificially created protrusions 220 as in FIG. 8a and/or cavities 221 as in FIG. 8b. These surface features 220, 221 can be distributed across the surface of the working electrode 122, in some variations the surface distribution can be fractal in nature. Similar surface area enlarging features, such as for example surface roughness, porosity, or the like can also optionally be used on the counter electrode.

Figure 9:
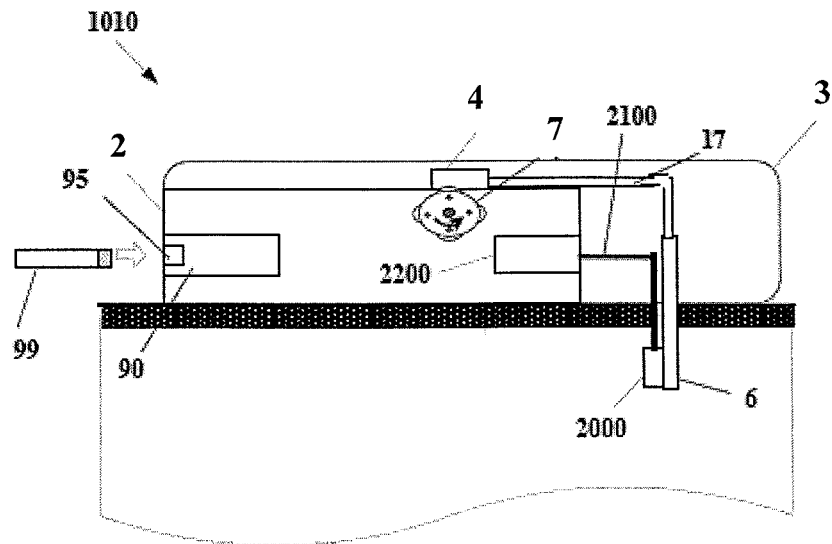
FIG. 9 is a schematic diagram showing a glucometer that uses a blood glucose test strip incorporated into an example device.

FIG. 9 shows another implementation of a fluid delivery device 1000 according to the current subject matter. In FIG. 9, the device 1000 is configured as a patch unit 1010, which also incorporates a glucometer or other blood analysis device 90. The patch unit 1010 can include a dispensing apparatus and a sensing apparatus, where the sensing apparatus, in addition to its ability to sense the analytes in the interstitial fluid (ISF), also includes the glucometer 90 that allows it to quantify one or more analytes in the blood. The glucometer 90 can be located in the reusable part 2 of the patch unit 1010. The user can extract blood from a remote location in the body and place the blood on a test strip 99. The test strip 99 can then be inserted into the glucometer 90 through a dedicated window 95 in the device housing.

In some variations, the glucometer (90) can serve as a calibration device contained within the patch unit 1010 of the device 1000. A continuous or semi-continuous glucose monitoring system can be calibrated relative to known glucose values determined using the glucometer 90 to maintain accurate glucose measurements throughout device operation. Alternatively or in addition a glucometer 90 can be located in the remote control unit 1008 of the fluid delivery device 1000. The glucometer in the remote control 1008 can be used in a similar manner to calibrate the glucose concentrations obtained from the in vivo sensing element 2000 in conjunction with the amperometric circuit 400.

Figure 10:
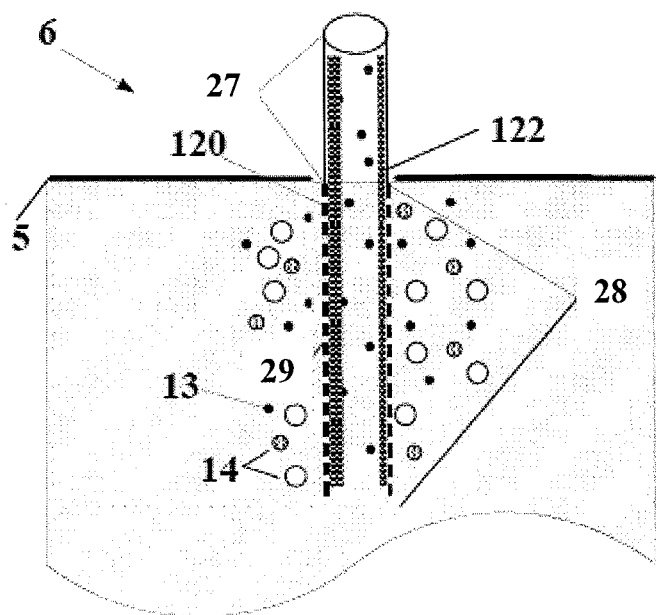
FIG. 10 is a schematic diagram showing an example of a semi-permeable cannula and the diffusion process.

FIG. 10 shows an example of a cannula 6 that can be used for sensing analyte concentration levels and for delivering fluid (dual function cannula). The cannula 6 has upper 27 and lower 28 portions that can be positioned, respectively, above and below the surface of the skin 5. The cannula 6 can be fitted with internal sensing electrodes 120, 122. The lower cannula portion 28 can include a semi-permeable membrane 29 that allows substances having low molecular weights, and particularly, of the desired analyte (such as for example glucose) 13 to pass through pores of the semi-permeable membrane 29, while molecules of substances 14 having of higher molecular weights are tend to not pass through the pores of the membrane 29. The cannula 6 can be perfused with an analyte-free solution (such as for example insulin or saline) to facilitate diffusion of analyte across the semi-permeable membrane 29 from the tissue fluid (such as for example the ISF) to the interior of the cannula 6. The diffusion process occurs in the direction of the concentration gradient, between the tissue fluid (ISF) and the solution within the cannula 6, until a partial or full analyte concentration equilibrium, or a "recovery" state, is established. Analyte concentration levels can be electrochemically measured using at least one working electrode 122 and at least one counter electrode 120 located within the subcutaneous cannula portion 28.

FIG. 11 shows another example of a dual function cannula 6 that has a membrane 30 having large pores that allow analyte diffusion across the membrane 30, such that the desired analyte (such as for example glucose) 13 and substances 14 of higher molecular weight pass through the larger pores. Such a cannula 6 allows fast analyte diffusion rate and shorter times for establishing the "recovery" state. Analyte concentration levels can be electrochemically measured using at least one working electrode 122 and at least one counter electrode 120 located within the subcutaneous cannula portion 28.

FIG. 12a and FIG. 12b show examples of cannulas 6 having a double lumen construction. The cannula 6 can include a sensing compartment or passage 60 and a dispensing compartment, passage, or lumen 70 that do not communicate with each other. The compartments or lumens can be separated by a wall. Monitoring analyte (e.g. glucose) levels can be carried out through the sensing compartment, passage, or lumen 60 which communicates with one or more sensing components as discussed above. The dispensing of fluid (e.g. insulin) can be carried out through the dispensing compartment, passage, or lumen 70 which communicates with one or more dispensing components as discussed above.

FIGS. 13-18 show several exemplary variations of a patch unit 1010 that can contain both sensing and dispensing components, with various configurations of subcutaneously insertable electrodes. In general, the insertable electrodes can include at least one working electrode, at least one counter electrode and optionally an additional reference electrode.

Components of the patch unit or external device 1000 in these implementations can include a reusable part 2 with a sensing processing element 2200, and a disposable part 3 with a reservoir 4, cannula 6, and delivery tube 17. On the outside surface of the cannula there can be two or more electrodes 120, 122, which are electrically connected by wiring 2100 to the sensing processing element 2200.

Figure 13A:
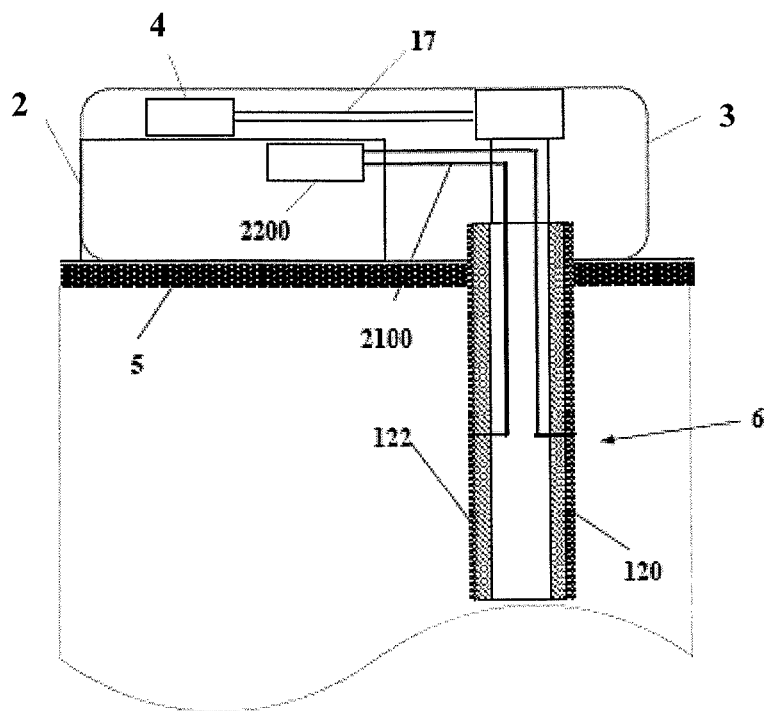
FIG. 13a and FIG. 13b are schematic diagrams showing side and transverse cross sections, respectively, of electrodes and the penetrating cannula associated with an example device for sensing an analyte and dispensing a therapeutic fluid.
Figure 13B:
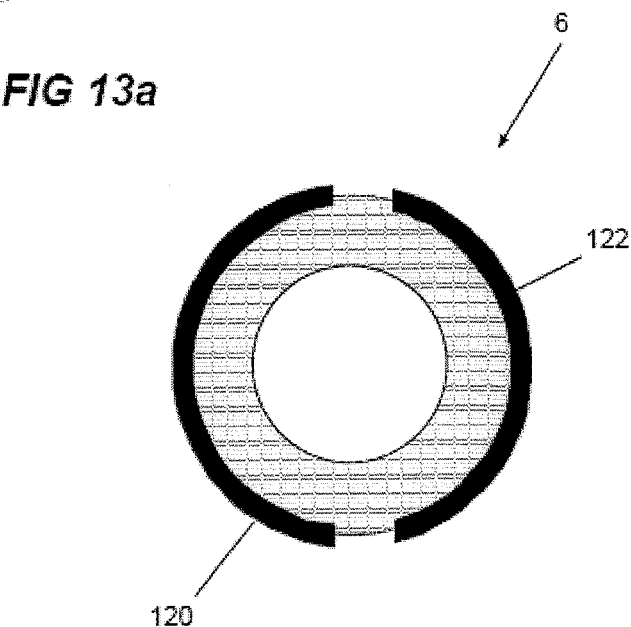

FIG. 13a and FIG. 13b show longitudinal and transverse cross sectional views, respectively of a cannula 6 with the electrodes 120, 122 extending along the entire length of the cannula 6. In some variations, the electrodes 120, 122 might extend only along a portion of the length of the cannula in a longitudinal direction or parallel with the longitudinal axis. In the example of FIG. 13a and FIG. 13b, the electrodes 120 and 122 can be formed as two or more electrically isolated sections of the outer walls of the cannula 6 and can include a working electrode, a counter electrode, and a optionally reference electrode such as for example as discussed above.

Figure 14A:
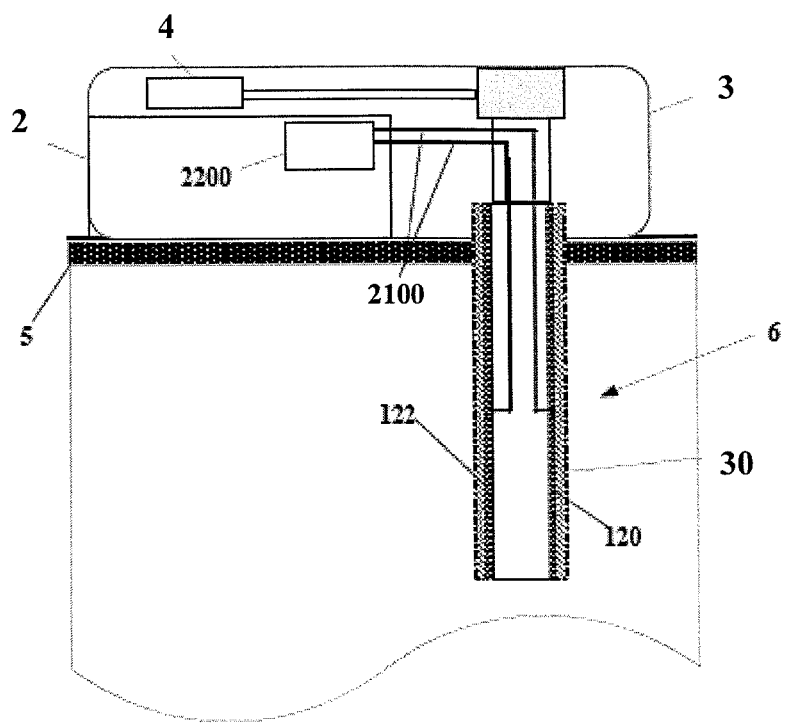
FIG. 14a and FIG. 14b are schematic diagrams showing side and transverse cross sections, respectively, of electrodes and the penetrating cannula associated with another device for sensing an analyte and dispensing a therapeutic fluid.
Figure 14B:
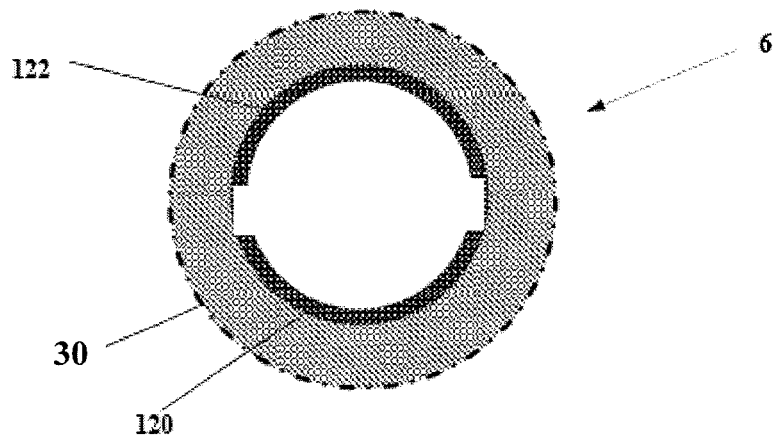

FIG. 14a and FIG. 14b show longitudinal and transverse cross sectional views, respectively, of a cannula 6 with the electrodes 120, 122 extending along the entire length of the cannula or along a region thereof. In this example, the counter and working electrodes 120, 122 are not positioned externally to the cannula as in the example of FIG. 13a and FIG. 13b. Rather, in FIG. 14a and FIG. 14b, the electrodes 120, 122 are positioned on electrically isolated internal surfaces of the cannula 6. The walls of the cannula 6 can be formed of a semi-permeable or permeable material that thus allows diffusion of the desired analyte into the interior of the cannula 6. The interior of the cannula 6 can function as a measurement cell.

Figure 15A:
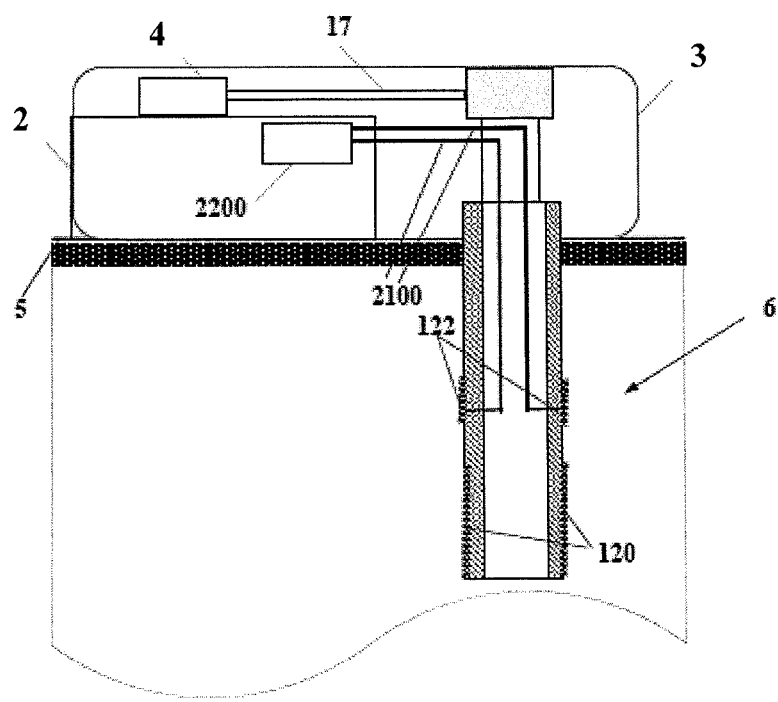
FIG. 15a and FIG. 15b are schematic diagrams showing a side cross section of a device and an expanded external view of a cannula, respectively, of another possible configuration of the electrodes and the penetrating cannula associated with a device for sensing an analyte and dispensing a therapeutic fluid.
Figure 15B:
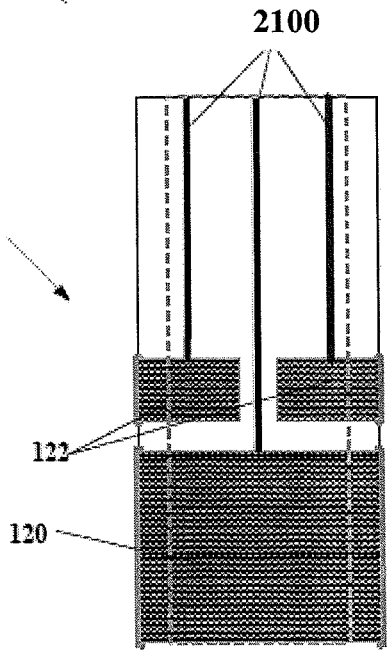

FIG. 15a and FIG. 15b show a longitudinal cross sectional view and a zoomed in outer surface view, respectively, of another example of a cannula 6 having electrodes 120, 122 located on the outer surface of the cannula 6. In this example, the electrodes 120, 122 can be disposed on the outer surface of the cannula 6. One electrode 120 can be disposed nearer the distal end of the cannula and electrically isolated, for example by an insulating material that could be used to form the structure of the cannula 6 itself. The second electrode 122 can be formed as a band that at least partly encircles the circumferential axis of the cannula 6. Wiring 2100 connects the electrodes 120, 122 to the sensor processing element 2200, which can be located in the reusable part 2 of the patch unit 1010 as discussed above.

Figure 16A:
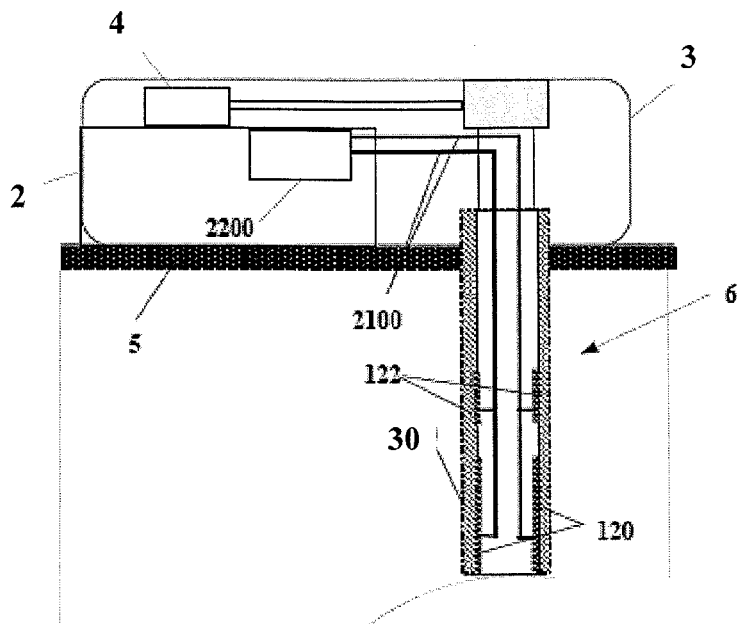
FIG. 16a and FIG. 16b are schematic diagrams showing a side cross section of a device and an expanded internal view of a cannula, respectively, of another possible configuration of the electrodes and the penetrating cannula associated with a device for sensing an analyte and dispensing a therapeutic fluid.
Figure 16B:
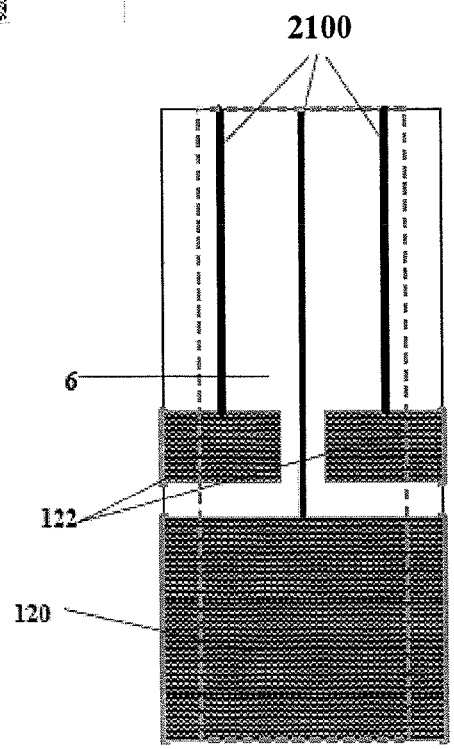

FIG. 16a and FIG. 16b show a longitudinal cross sectional view and a zoomed in inner surface view, respectively, of another example of a cannula 6 having working 122 and counter 120 electrodes located on the inner surface of the cannula 6. The walls of the cannula can be semi-permeable or permeable to allow analytes to enter the measurement cell formed within the cannula 6.

Figure 17A:
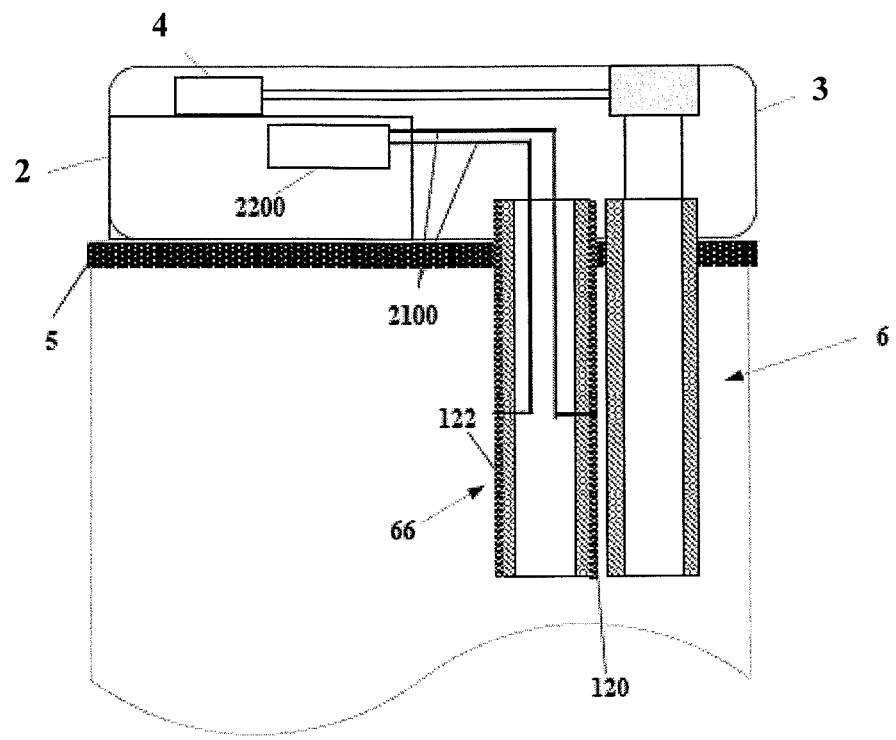
FIG. 17a and FIG. 17b are schematic diagrams showing a side cross section and a transverse cross section of a sensing cannula for a device for sensing an analyte and dispensing a therapeutic fluid and including two cannulae.
Figure 17B:
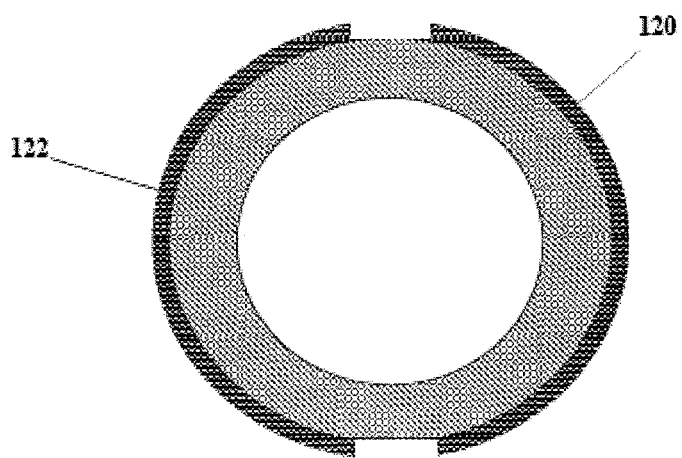
Figure 18A:
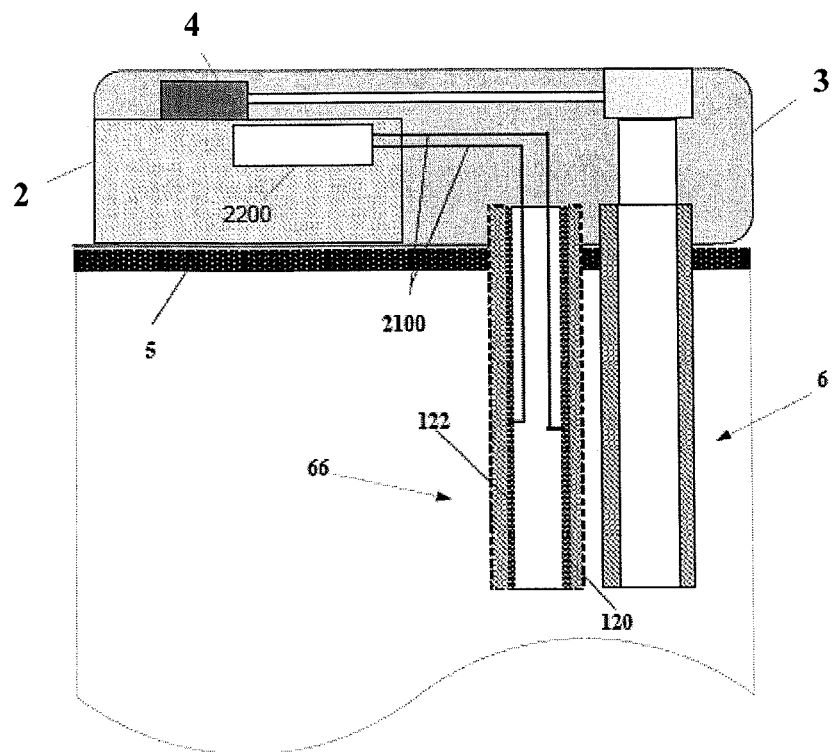
FIG. 18a and FIG. 18b are schematic diagrams showing a side cross section and a transverse cross section of a sensing cannula for another device for sensing an analyte and dispensing a therapeutic fluid and including two cannulae.
Figure 18B:
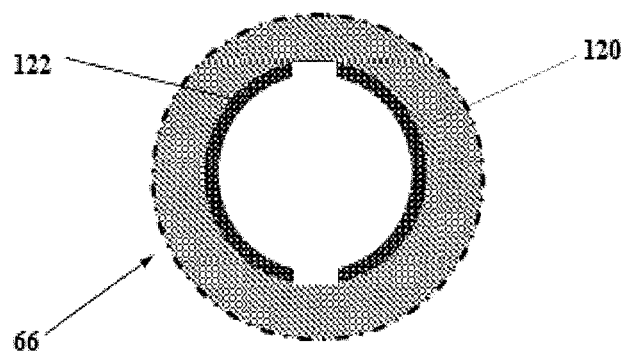

FIGS. 17 and 18 show examples of patch units 1010 that include two cannulae 6, 66. A first cannula 6 can be used for sensing the analyte and a second cannula 66 can be used for dispensing therapeutic fluid. FIG. 17a and FIG. 18a show longitudinal views of the two implementations, and FIG. 17b and FIG. 18b show cross sectional views of the two implementations. In FIG. 17, the electrodes are disposed on the outer surface of the cannula 6 and oriented along at least part of the longitudinal axis of the cannula 6. In FIG. 18 the electrodes 120, 122 are disposed on the inner surface of a cannula 6 whose walls can be semi-permeable or permeable over at least some area of the wall.

Figure 19:
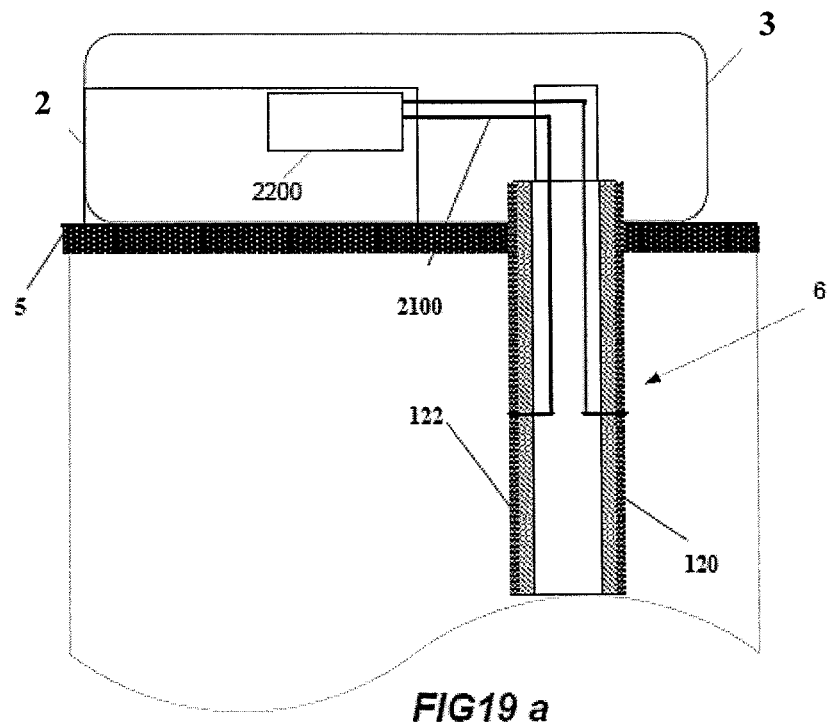
FIG. 19a and FIG. 19b are schematic diagrams showing side and transverse cross sections, respectively, of electrodes associated with a sensing probe employed in a device for sensing an analyte only.
Figure 19B:
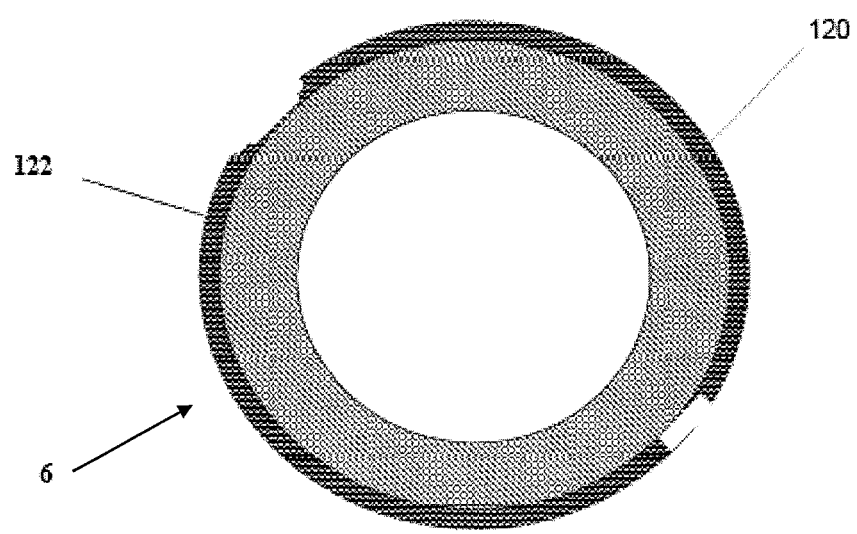
Figure 20A:
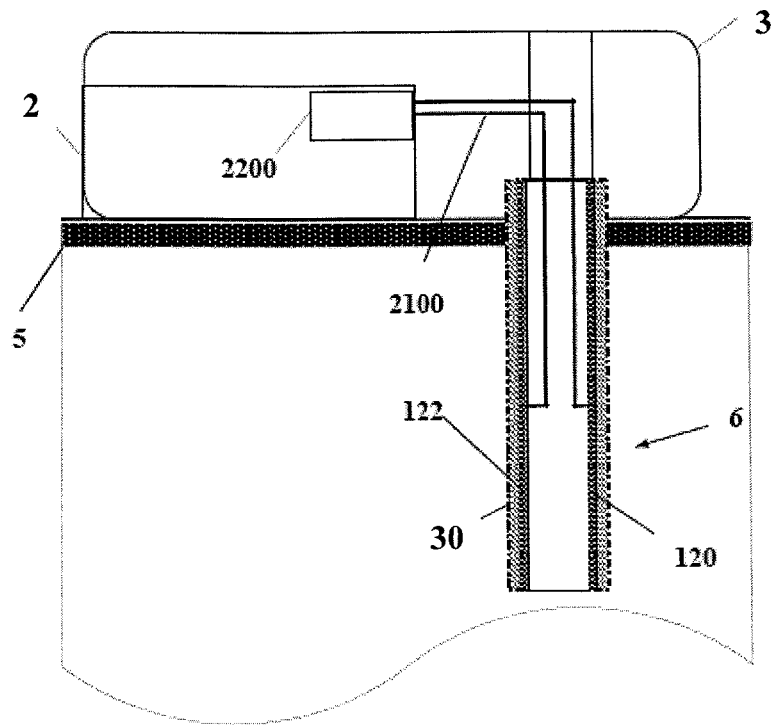
FIG. 20a and FIG. 20b are schematic diagrams showing side and transverse cross sections, respectively, of electrodes associated with a sensing probe employed in another device for sensing an analyte only.
Figure 20B:
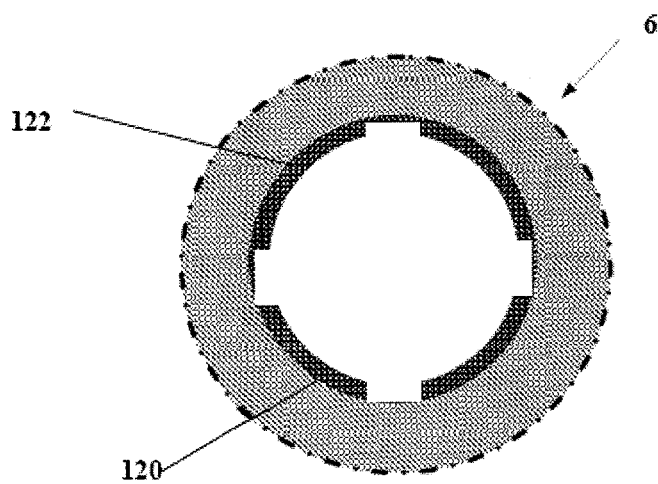

FIGS. 19 and 20 show examples of patch units 1010 that include only a sensing apparatus (stand-alone sensor). These devices can be used for sensing of in vivo analyte concentrations. FIG. 19a and FIG. 19b show longitudinal and transverse cross sectional views, respectively, of the working 122 and counter 120 electrodes extending along the entire or partial length (not shown) of the outer surface of the cannula 6. FIG. 20a and FIG. 20b show longitudinal and transverse cross sectional views, respectively, of the four electrodes 120, 122 extending along the entire or partial length (not shown) of the inner surface of the cannula 6. The cannula 6 walls can be semi-permeable or permeable along all or part of the surface area of the cannula that penetrates the skin 5.

Figure 21:
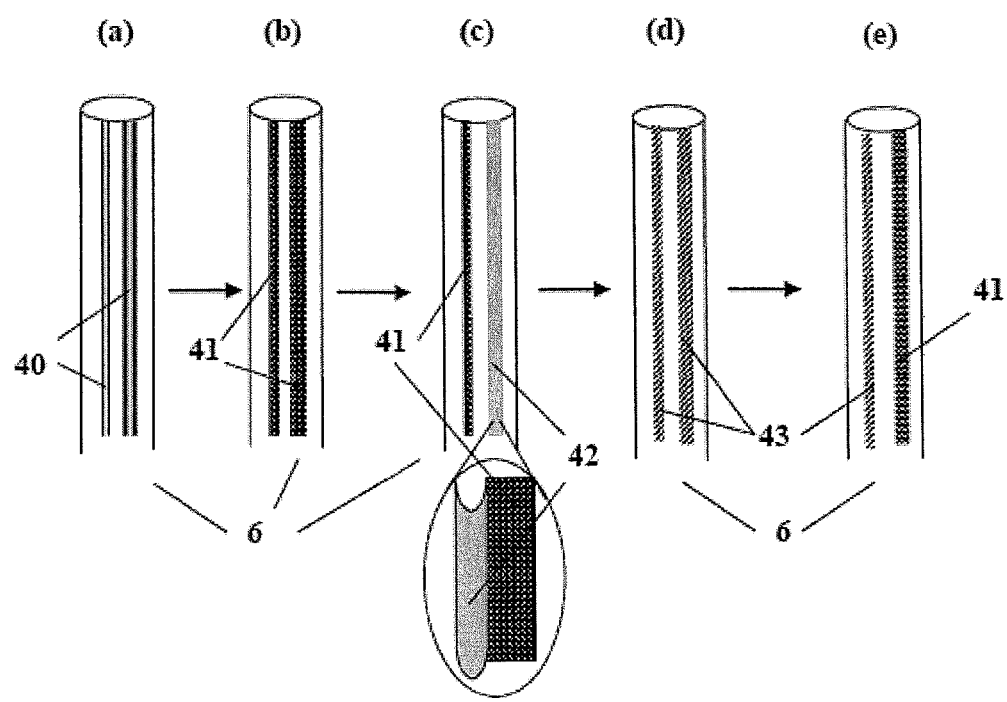
FIG. 21 is a diagram showing possible stages in a process of manufacturing of a sensing probe.

FIG. 21 illustrates a possible process for fabrication of electrodes on the outer or inner surface of a cannula 6. This process can include formation of two grooves 40 on the cannula 6 surface, such as for example as shown in FIG. 21a. The grooves can be filled with conductive material 41 as shown in FIG. 21b. Electrodes can alternatively be deposited on the external surface of the cannula 6 by vapor deposition, sputtering, painting, printing, replication, electro-less deposition, or any other method now known or hereafter developed. Electrodes can be deposited on inner surfaces of the cannula 6 by sputtering, painting, replication, electro less deposition, or any other method now known or hereafter developed. One of the electrodes can be temporarily covered. For example the counter electrode can be covered with a removable protective layer 42 as shown in FIG. 21c. The protective layer 42 can be any adherable material that is not penetrable. All of the electrodes can then be covered with electrochemical reagents 43 (such as for example an enzyme, a mediator, or the like) as shown in FIG. 21d. The protective layer 42 can be pealed from the counter electrode as shown in FIG. 21e. At the end of the fabrication process, the working electrodes can be formed. The working electrode can be loaded or otherwise coated with one or more electrochemical reagents while the counter electrodes are free of the electrochemical reagents. After pealing the protective layer from the counter electrode, only the working electrode carries electrochemical reagents.

Figure 22:
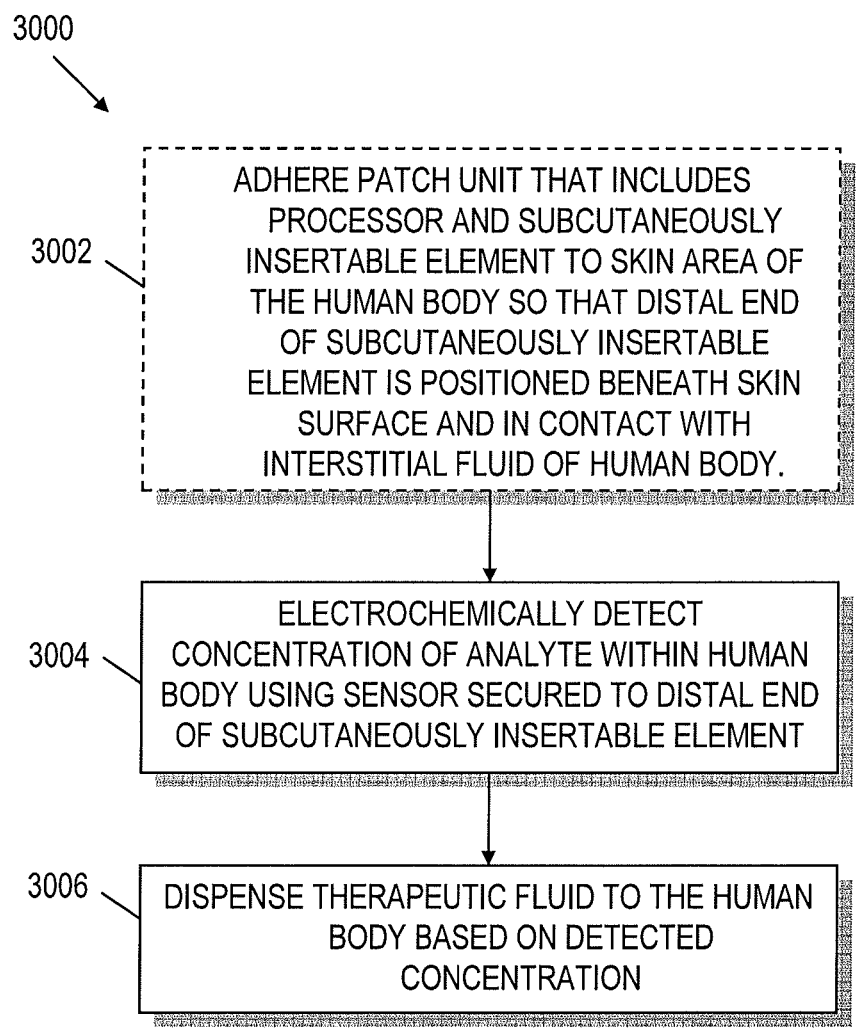
FIG. 22 is a process flow diagram showing a method for monitoring and controlling the concentration of an analyte in a body.

FIG. 22 is a process flow chart 3000 that shows stages of a method for sensing and controlling blood glucose levels using a closed loop device. At 3002, a patch unit that includes a processor and a subcutaneously insertable element can optionally be adhered or secured to a skin area of the human body such that a distal end of the subcutaneously insertable element is positioned beneath the skin surface and in contact with interstitial fluid of human body. The adhering or securing can optionally be by means of an adhesive, by suction, by one or more hooks that grasp a portion of the skin surface, or the like. As described above, the proximal end of the subcutaneously insertable element can be part of or mechanically connected to the patch unit or other mechanical device. At 3004, the concentration of an analyte within the human body can be electrochemically detected using a sensor that is secured to or otherwise associated with the distal end of the subcutaneously insertable element. This electrochemical detection can optionally be accomplished by generating a signal that represents the concentration at the sensor, possibly by means of an enzymatic reaction as discussed above. The signal can optionally be received and processed at a processor in the external device or patch unit. If the concentration is determined to be outside of a target concentration range, therapeutic fluid can be dispensed to the human body at 3006. Dispensing of the therapeutic fluid can optionally include delivering a command from the processor to a dispensing apparatus in the external device. The dispensing apparatus can be one of those as described above or other similar structures. The command can cause the dispensing apparatus to dispense an amount of the therapeutic fluid sufficient to alter the concentration of the analyte in the human body so that the concentration returns to within the target range.

The implementations set forth in the foregoing description do not represent all implementations consistent with the subject matter described herein. Instead, they are merely some examples consistent with aspects related to the described subject matter. Other aspects, advantages, and modifications are considered to be within the scope of the claims presented below. The claims presented are representative of the subject matter disclosed herein. Other, unclaimed aspects of the disclosed subject matter are also contemplated.

Wherever possible, the same reference numbers have been used throughout the drawings to refer to the same or like parts. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

What is claimed:

1. An apparatus comprising:
   a subcutaneously insertable element that comprises a proximal portion and a distal portion, the distal portion being configured for subcutaneous placement within the body of a patient, the subcutaneously insertable element comprising a cannula having an internal volume and a wall surface;
   a sensor that interacts with one or more analytes and generates a signal that is representative of a concentration of the one or more analytes, the sensor comprising a first electrode and a second electrode electrically isolated from the first electrode, the first electrode and second electrode being secured to the cannula;
   a pump for delivering a therapeutic fluid through the distal portion of the subcutaneously insertable element via a flow path from a reservoir configured to contain the therapeutic fluid to the subcutaneously insertable element;
   a processor for receiving the signal from the sensor and for determining the concentration of the one or more analytes within the body of the patient based on the signal, the processor receiving the signal via at least one continuous electrical signal path between the distal end of the subcutaneously insertable element and the processor; and
   an external device comprising a single housing or at least two physically connected housings containing the pump, the processor, the reservoir, and the at least one continuous electrical signal path between the proximal end of the subcutaneously insertable element and the processor, the proximal portion of the subcutaneously insertable element being in direct physical contact with the single housing or one of the at least two physically connected housings,
   wherein the sensor is disposed within the distal portion of the subcutaneously insertable element, with the first electrode and the second electrode being disposed on an inner surface of the cannula, and with at least part of the wall surface of the cannula being permeable or semipermeable.

2. The apparatus of claim 1, wherein one or more of the first and second electrodes is disposed along at least part of a circumferential axis of the cannula.

3. The apparatus of claim 1, wherein one or more of the first and second electrodes is disposed along at least part of a longitudinal axis of the cannula.

4. The apparatus of claim 1, wherein the first electrode comprises a first exposed surface that is at least partially coated with an electrochemical reagent and the second electrode comprises a second exposed surface that is substantially free of the electrochemical reagent.

5. The apparatus of claim 4, wherein the electrochemical reagent comprises an enzymatic assay that undergoes a chemical reaction with the one or more analytes, the chemical reaction producing a measurable voltage or current differential between the first electrode and the second electrode.

6. The apparatus of claim 4, wherein the first and/or the second exposed surface comprise one or more surface area enlarging features.

7. The apparatus of claim 1, wherein the pump flushes the subcutaneously insertable element with the therapeutic fluid from the reservoir.

8. The apparatus of claim 1, wherein the external device comprises at least two physically connected housings, the at least two physically connected housings comprising a disposable part housing and a reusable part housing, the disposable part housing containing the reservoir and being in direct physical contact with the proximal portion of the subcutaneously insertable element, and the reusable part containing the processor and at least a portion of the pump.

9. The apparatus of claim 8, wherein the reusable part housing contains at least one first electrical conducting element forming a first continuous electrical path between the processor and at least one first electrical contact, the disposable part housing contains at least one second electrical conducting element forming a second continuous electrical path between the sensor and at least one second electrical contact, and the at least one first electrical contact connects to the at least one second electrical contact to form the at least one continuous electrical signal path when the disposable part housing and the reusable part housing are connected.

10. The apparatus of claim 1, wherein the pump is configured to deliver the therapeutic fluid based on the concentration of the one or more analytes determined by the processor.

11. The apparatus of claim 1, wherein the subcutaneously insertable element comprises a first lumen that comprises the sensor at the distal end of the subcutaneously insertable element and a second lumen through which the therapeutic fluid is delivered.

12. The apparatus of claim 1, wherein the processor automatically controls the pump based on the determined concentration.

13. The apparatus of claim 1, wherein the external device further comprises a blood analysis device in communication with the processor and a port via which a blood sample from the body is delivered to the blood analysis device, the blood analysis device analyzing the blood sample to independently determine the concentration of the one or more analytes.

14. The apparatus of claim 1, wherein the apparatus is capable of operating in one or more of a closed loop mode, an open loop mode and a semi-open loop mode.

15. The apparatus of claim 1, wherein at least one of the pump and the sensor is controllable by a remote control.

16. The apparatus of claim 1, wherein the therapeutic fluid comprises insulin and the one or more analytes comprises glucose.

17. The apparatus of claim 1, wherein the flow path between the pumping mechanism and the proximal portion of the subcutaneously insertable element comprises a delivery tube that is contained within the single housing or the at least two physically connected housings.

18. The apparatus of claim 1, wherein the proximal portion of the subcutaneously insertable element is associated with a skin-facing side of the single or at least two physically connected housings.

19. The apparatus of claim 1, wherein the external device comprises at least two physically connected housings, the at least two physically connected housings comprising a disposable part housing and a reusable part housing, the reusable part containing the processor, at least a portion of the pumping mechanism, at least one first electrical contact, and at least one first electrical conducting element forming a first continuous electrical path between the processor and the at least one first electrical contact; the disposable part housing being in direct physical contact with the proximal portion of the subcutaneously insertable element and containing at least one second electrical contact and at least one second electrical conducting element forming a second continuous electrical path between the sensor and the at least one second electrical contact, the at least one first electrical contact connecting to the at least one second electrical contact to form the at least one continuous electrical signal path when the disposable part housing and the reusable part housing are connected.

20. A method comprising:
detecting, with a sensor secured to a distal end of a subcutaneously insertable element, a concentration of one or more analytes within a body of a patient, the subcutaneously insertable element comprising a proximal end opposite to the distal end, the proximal end being in direct physical contact with a single housing or one of at least two physically connected housings of an external device, the single housing or the at least two physically connected housings containing a reservoir containing a therapeutic fluid, a pump, a processor, and at least one continuous electrical signal path between the proximal end of the subcutaneously insertable element and the processor; and dispensing a therapeutic fluid to the body of the patient through a cannula of the subcutaneously insertable element, the dispensing occurring by action of the pump and via a flow path between the reservoir and the cannula;
wherein the sensor comprises a first electrode and second electrode each being disposed on an inner surface of the subcutaneously insertable element, and wherein at least part of a wall surface of the cannula is permeable or semi-permeable.

21. The method of claim 20, further comprising:
securing the external device to a skin surface of the patient such that the distal end of the subcutaneously insertable element is positioned beneath the skin surface and in contact with interstitial fluid of the body of the patient.

22. The method of claim 20, wherein:
the detecting comprises generating a signal at the sensor that is representative of the concentration, receiving and processing the signal at the processor, the processing of the signal comprising determining the concentration of the one or more analytes; and
the dispensing of the therapeutic fluid comprises delivering a command from the processor to the pumping mechanism, the command causing the pumping mechanism to dispense an amount of the therapeutic fluid based on the determined concentration of the one or more analytes.

23. The method of claim 20, wherein the sensor is part of a closed loop system and the dispensing is carried out automatically based on the detected concentration.

24. An apparatus for delivering insulin to a body of a patient and for sensing glucose, the apparatus comprising:
a cannula that comprises a proximal portion and a distal portion, the distal portion configured for subcutaneous placement within the body of the patient, the cannula further comprises a wall surface and an internal volume;
a sensor that electrochemically interacts with glucose and generates a signal that is representative of a glucose concentration, the sensor disposed within the distal portion of the cannula; and
a patch unit securable to a body of a patient, the patch unit including:
a reusable part housing containing at least a portion of a pump for delivering insulin from a reservoir into the body of the patient through the cannula, a processor that receives and processes the signal from the sensor to determine the glucose concentration within the body of the patient, and at least one first electrical conducting element forming a first continuous electrical path between the processor and at least one first electrical contact in the reusable part housing, the processor being configured to control the pump to deliver the insulin based on the glucose concentration determined by the processor; and
a disposable part housing in direct physical contact with the proximal portion of the cannula and containing at least one second electrical conducting element forming a second continuous electrical path between the sensor and at least one second electrical contact in the disposable part housing, the at least one second electrical contact being configured to connect to the at least one first electrical contact to form a completed electrical path between the sensor and the processor when the disposable part housing and the reusable part housing are connected to enable operation of the patch unit;
wherein the sensor comprises a first electrode and a second electrode electrically isolated from the first electrode, the first electrode and second electrode being secured to the cannula, and with at least part of the wall surface of the cannula being permeable or semi-permeable.

25. The apparatus of claim 24, wherein the second continuous electrical path between the sensor and at least one second electrical contact in the disposable part housing further comprises at least one third electrical contact in the disposable part housing that is configured to connect to at least one fourth electrical contact in the proximal portion of the cannula, the at least one fourth electrical contact further connecting to at least one fourth electrical conducting element that provides a connection to the sensor.

\* \* \* \* \*